US012293524B2

United States Patent
Groth et al.

(10) Patent No.: US 12,293,524 B2
(45) Date of Patent: May 6, 2025

(54) PREDICTING CORRECTNESS OF ALGORITHMIC SEGMENTATION

(71) Applicant: KONINKLIJKE PHILIPS N.V., Eindhoven (NL)

(72) Inventors: Alexandra Groth, Hamburg (DE); Rolf Jurgen Weese, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 689 days.

(21) Appl. No.: 17/287,142

(22) PCT Filed: Oct. 14, 2019

(86) PCT No.: PCT/EP2019/077684
§ 371 (c)(1),
(2) Date: Apr. 21, 2021

(87) PCT Pub. No.: WO2020/083676
PCT Pub. Date: Apr. 30, 2020

(65) Prior Publication Data
US 2021/0390707 A1 Dec. 16, 2021

(30) Foreign Application Priority Data
Oct. 22, 2018 (EP) ..................................... 18201798

(51) Int. Cl.
*G06T 7/12* (2017.01)
*G06N 5/022* (2023.01)
*G16H 30/40* (2018.01)

(52) U.S. Cl.
CPC ............... *G06T 7/12* (2017.01); *G06N 5/022* (2013.01); *G16H 30/40* (2018.01); *G06T 2207/20081* (2013.01); *G06T 2207/30048* (2013.01)

(58) Field of Classification Search
CPC ............. G06T 7/12; G06T 2207/20081; G06T 2207/30048; G06T 7/11; G06N 5/022; G16H 30/40
(Continued)

(56) References Cited

U.S. PATENT DOCUMENTS

| | | | |
|---|---|---|---|
| 9,483,866 B2 | 11/2016 | Stetson | |
| 9,665,941 B2 | 5/2017 | Tang | |
| 9,767,569 B2 | 9/2017 | Jo et al. | |
| 10,147,185 B2 | 12/2018 | Riklin Raviv | |
| 10,546,014 B2 | 1/2020 | Han | |
| 11,715,206 B2 | 8/2023 | Yu | |

(Continued)

FOREIGN PATENT DOCUMENTS

| | | | |
|---|---|---|---|
| CN | 107749061 A | 3/2018 | |
| CN | 1077673781 B | * 3/2018 | ........... G06T 7/0012 |

(Continued)

OTHER PUBLICATIONS

Ecobert et al: "Segmentation of the Heart and Great Vessels in CT Images Using a Model-Based Adaptation Framework"; Medical Image Analysis 15 (2011), pp. 863-876.
(Continued)

*Primary Examiner* — Jerome Grant, II (57) ABSTRACT

A prediction model is provided which is capable of predicting a correctness of a segmentation by a segmentation algorithm. The prediction model may be trained using a machine learning technique, and after training used to predict the correctness of a segmentation of a boundary in respective image portions of an image by the segmentation algorithm. The predicted correctness may then be visualized, for example as an overlay of the segmentation.

14 Claims, 5 Drawing Sheets

(58) Field of Classification Search
USPC .......................................................... 382/128
See application file for complete search history.

(56) References Cited

U.S. PATENT DOCUMENTS

| | | |
|---|---|---|
| 2006/0210158 A1 | 9/2006 | Pekar |
| 2014/0247977 A1 | 9/2014 | Han |
| 2017/0337689 A1 | 11/2017 | Li |
| 2018/0061059 A1 | 3/2018 | Xu et al. |
| 2018/0089834 A1 | 3/2018 | Spizhevoy et al. |

FOREIGN PATENT DOCUMENTS

| | | | | |
|---|---|---|---|---|
| EP | 3379281 | * | 9/2018 | ............. G01R 33/56 |
| WO | 2012073151 A2 | | 6/2012 | |
| WO | WO2018015414 | * | 1/2018 | ............... G06K 9/00 |
| WO | 2018-038748 A1 | | 3/2018 | |
| WO | 2018119358 A1 | | 6/2018 | |
| WO | WO2020031243 | * | 2/2020 | ............... G06T 7/11 |

OTHER PUBLICATIONS

Frounchi et al: "Automating Image Segmentation Verification and Validation by Learning Test Oracles"; Information and Software Technology 53 (2011), pp. 1337-1348.
PCT/EP2019/077684 ISR & WO, Nov. 7, 2019, 16 Page Document.
Kronman et al: "A Geometric Method for the Detection and Correction of Segmentation Leaks of Anatomical Structures in Volumetric Medical Images"; Int J Cars (2016), vol. 11, pp. 369-380.

* cited by examiner

PREDICTING CORRECTNESS OF ALGORITHMIC SEGMENTATION

CROSS-REFERENCE TO PRIOR APPLICATIONS

This application is the U.S. National Phase application under 35 U.S.C. § 371 of International Application No. PCT/EP2019/077684, filed on Oct. 14, 2019, which claims the benefit of European Patent Application No.18201798.8, filed on Oct. 22, 2018 These applications are hereby incorporated by reference herein.

FIELD OF THE INVENTION

The invention relates to systems and computer-implemented methods in the field of image segmentation, such as image segmentation of anatomical structures in medical images. The invention further relates to a computer-readable medium comprising instructions to perform a computer-implemented method.

BACKGROUND OF THE INVENTION

Image segmentation is widely used in various field, including but not limited to the medical field. In the latter example, image segmentation is often used to identify anatomical structures in medical images, e.g., by delineating the boundaries of the anatomical structure, by labelling of the voxels enclosed by the boundaries, etc. Once such segmentation has been performed, it is possible to extract clinical parameters such as, in case of, e.g., a cardiac structure, ventricular mass and wall thickness. Such segmentation is frequently also referred to as delineation or annotation, and may identify the external boundary surfaces of an anatomical structure, but also internal surfaces of said anatomical structure.

It is known to perform segmentation using meshes. Such meshes may be applied automatically, manually or semi-automatically to a medical image. The automatic or semi-automatic application may involve the use of an adaptation technique, also termed 'mesh adaptation' or 'mesh fitting'. The adaptation technique may, for example, optimize an energy function based on an external energy term which adapts the mesh to the image data and an internal energy term which maintains a rigidness of the mesh. Various adaptation techniques are known for automatically applying meshes to medical images. An example of an automatic technique is described in "SEGMENTATION OF THE HEART AND GREAT VESSELS IN CT IMAGES USING A MODEL-BASED ADAPTATION FRAMEWORK" by O. Ecabert et al., Medical Image Analysis, Volume 15, Issue 6, December 2011, pages 863-876, which describes the automatic segmentation of the heart from three-dimensional (3D) Computed Tomography (CT) images. An applied mesh may also be displayed together with the medical image to visualize information, such as the shape and location of the anatomical structure. For example, the mesh may be shown as an overlay over the anatomical structure in the medical image.

Other forms of segmentation are equally known. For example, a Convolutional Neutral Network may provide a pixel or voxel-wise annotation, which may then be converted into a mesh or other type of surface representation, e.g., using the Marching Cubes algorithm or using morphological operations.

As indicated earlier, the segmentation result, e.g., the applied mesh, may be used for measurements (e.g., left ventricular volume over the heart cycle), for diagnosis, for treatment planning (e.g., aortic valve implant fitting), for the prediction of diseases (e.g., as input for biophysical models), etc. However, in some cases, the segmentation by a segmentation algorithm may not be fully correct. For example, the mesh may be inaccurately applied to the boundary of the anatomical structure, and may thereby be insufficiently accurate for its purpose, e.g., to serve for measurements, diagnostic purposes, treatment planning, disease prediction, etc.

It may therefore be needed for a user to locally correct the segmentation provided by a segmentation algorithm. For example, a user may edit an applied mesh using a view of the image and the applied mesh. The view may show a part of the mesh which is to be edited. The mesh editing itself may involve, e.g., re-positioning of a mesh part, increasing the resolution of a mesh part, etc.

Disadvantageously, it is time consuming and tedious work to inspect every part of the segmentation to determine whether it requires correction or not.

SUMMARY OF THE INVENTION

It may be desirable to avoid or reduce the need for a user to inspect every part of the segmentation provided by a segmentation algorithm.

The following aspects of the invention may involve generating a prediction model for predicting a correctness of a segmentation by a segmentation algorithm. The prediction model may be trained using a machine learning technique, and after training used to predict the correctness of a segmentation of a boundary in respective image portions of an image by the segmentation algorithm. The predicted correctness may then be visualized, for example as an overlay of the segmentation.

In accordance with a first aspect of the invention, a system may be provided for generating a prediction model for predicting a correctness of segmentation by a segmentation algorithm.

The system may comprise:
a data interface for accessing:
   training image data;
   labels for respective image portions of the training image data, wherein the labels are obtained by applying the segmentation algorithm to the training image data, wherein the labels are indicative of a correctness of the segmentation of a boundary in the respective image portion by the segmentation algorithm;
a processor subsystem configured to:
   train the prediction model using a machine learning technique and using said labelled image portions as input; and
   output model data representing the trained prediction model.

In accordance with a further aspect of the invention, a computer-implemented method may be provided for generating a prediction model for predicting a correctness of segmentation by a segmentation algorithm.

The method may comprise:
accessing:
   training image data;
   labels for respective image portions of the training image data, wherein the labels are obtained by applying the segmentation algorithm to the training image data, wherein the labels are indicative of a correctness of the segmentation of a boundary in the respective image portion by the segmentation algorithm;

training the prediction model using a machine learning technique and using said labelled image portions as input; and outputting model data representing the trained prediction model.

In accordance with a further aspect of the invention, a system may be provided for predicting a correctness of segmentation by a segmentation algorithm.

The system may comprise:

a data interface for accessing:

model data representing a prediction model which is trained on labelled image portions of training image data, wherein labels of the labelled image portions are indicative of a correctness of segmentation of a boundary in the respective image portion by the segmentation algorithm; and input image data containing a boundary to be segmented by the segmentation algorithm;

a processor subsystem configured to:

apply the prediction model to respective image portions of the input image data to predict the correctness of the segmentation of the boundary in the respective image portions by the segmentation algorithm; and generate output data indicative of the correctness of segmentation to enable an incorrect segmentation of the boundary by the segmentation algorithm to be identified on the basis of the output data.

In accordance with a further aspect of the invention, a computer-implemented method may be provided for predicting a correctness of segmentation by a segmentation algorithm.

The method may comprise:

accessing:

model data representing a prediction model which is trained on labelled image portions of training image data, wherein labels of the labelled image portions are indicative of a correctness of segmentation of a boundary in the respective image portion by the segmentation algorithm; and input image data containing a boundary to be segmented by the segmentation algorithm;

applying the prediction model to respective image portions of the input image data to predict the correctness of the segmentation of the boundary in the respective image portions by the segmentation algorithm; and generating output data indicative of the correctness of segmentation to enable an incorrect segmentation of the boundary by the segmentation algorithm to be identified on the basis of the output data.

The above measures involve training a prediction model to provide a prediction of the correctness of segmentation by segmentation algorithm, and subsequently using the prediction model to provide a prediction of correctness, for example during use of the segmentation algorithm in clinical practice or elsewhere.

The following refers to effects and advantages when these measures are applied in the clinical or medical field. It will be appreciated, however, that the effects and advantages manifest themselves also in other fields, mutatis mutandis.

At the training side, e.g., when generating the prediction model, training image data is provided, which may for example be comprised of a set of medical images. Additionally, labels are provided which are indicative of a correctness of the segmentation of a boundary in respective image portions in the training image data when the segmentation algorithm is applied to the training image data. Here, the term 'correctness' may refer to a qualification of the segmentation, which may for example include a binary qualification ('correct' or 'incorrect', 'correction needed' or 'correction not needed', etc.) or a non-binary qualification (e.g., a scale of 0 to 10, a quantification of the difference between the segmentation and the actual boundary, e.g., in millimetres, etc), etc. The labels may directly specify the correctness but also indirectly, e.g., as described elsewhere.

Such labels may be generated in various ways, e.g., automatically, manually or semi-automatically. Automatic ways of generating the labels are described elsewhere in this specification. In general, however, the generating of the labels may involve applying the segmentation algorithm to the training image data, determining the correctness of segmentation and then assigning labels to the image portions which are indicative of the correctness of segmentation.

The prediction model, which may for example take the form of a Convolutional Neural Network, may then be trained on the labelled image portions using a machine learning technique as known per se. The prediction model may then be made available for subsequent use by outputting the model's data.

At the application side, e.g., when using the prediction model on non-training input image data, such as one or more input images, the prediction model may be applied to respective image portions of the input image data to predict the correctness of the segmentation of a boundary in the respective image portions by the segmentation algorithm. Such prediction may effectively generate same or similar labels for respective image portions as were used during the training of the prediction model. Having predicted the correctness, output data may be generated which is indicative of the predicted correctness so as to enable an incorrect segmentation of the boundary by the segmentation algorithm to be identified on the basis of the output data. For example, an output image may be generated which visualizes the predicted correctness as an overlay over the segmentation itself.

In this respect, it is noted that although typically the segmentation algorithm is actually applied to the input image data at the application side, this is not needed per se to predict the correctness of the segmentation since the prediction model uses the input image data as input and not the segmentation itself.

The above measures have as effect that a prediction of the correctness of a segmentation is obtained which may be used to highlight or in another way identify image portions in which the segmentation may be incorrect, or at least insufficiently correct. The segmentation in such image portions may have to be inspected, and likely to be corrected, by a user. When identifying such image portions to a user, it is therefore not, or only to a lesser degree, needed for a user to inspect the entire segmentation, e.g., all parts of an applied mesh.

Effectively, knowledge on the imperfections or limitations of a segmentation algorithm may be encoded, by way of machine learning, in a prediction model and subsequently used at the application side to identify image portions in which the segmentation may necessitate inspection and/or correction.

The following optional aspect relate to the system and computer-implemented method of generating, e.g., training, the prediction model.

Optionally, the processor subsystem is further configured to generate the labels for the respective image portions by:

via the data interface, accessing:

first segmentation data representing the segmentation of the boundary in the respective image portions by the segmentation algorithm;

second segmentation data representing a corrected segmentation of the boundary in the respective image portions by a user;

determining the correctness of segmentation by comparing the first segmentation data with the second segmentation data; and assigning the labels which are indicative of the correctness of segmentation to the respective image portions.

The labels may be generated (semi)automatically by obtaining a segmentation of the boundary by the segmentation algorithm and the (same) segmentation after inspection and correction by a user. Any differences between both segmentations may thus represent corrections by a user, and therefore may be indicative of the original segmentation by the segmentation algorithm being incorrect, or at least insufficiently correct. The image portions of the image to which the segmentation pertains may each be labelled by locally comparing both segmentations and quantifying the difference to generate the label. Here, the term 'image portion' may refer to a part of the image, such as a sub-volume, an image patch, etc. The image portions may or may not mutually overlap. All of the training image data may be labelled in the abovementioned manner. Labels may be assigned in any known manner, e.g., as metadata in the image data or as separate metadata. For example, any known technique for assigning annotations to an image may be used, as is known per se from the field of image annotation.

The above manner of generating labels is based on the recognition that sets of segmentations and corrected segmentations may exist in the clinical field. Namely, the segmentations may have been generated and subsequently corrected during clinical practice to ensure sufficient quality of the segmentation for the intended clinical purpose. It may therefore not be needed for a user to explicitly review segmentation results and label the segmentations for the sole purpose of generating the training image data. Rather, re-use may be made of existing image data and segmentation data to generate labelled image data for training purposes.

Optionally, the processor subsystem is configured to determine the correctness of the segmentation by the segmentation algorithm for an image portion based on a distance between corresponding parts of the respective segmentations of the boundary. The distance between corresponding parts of the respective segmentations of the boundary may be readily determined, e.g., as a geometric distance between the centres of corresponding meshes of both segmentations or in any other known manner, and may be indicative of the correctness of the segmentation. Namely, if the distance is zero, no correction took place, which is an indication that the original segmentation was correct. Conversely, if there is a non-zero distance, this may indicate that a correction took place. Moreover, the size of the distance may be indicative of the quality of the original segmentation, e.g., a large distance may represent a large correction and may indicate an originally poor segmentation, whereas a small distance may represent a small correction and may indicate an originally imperfect but still reasonable segmentation. In some embodiments, the distance, e.g., as expressed in millimetres or any other suitable unit, may be used directly as the label for a respective image portion.

The following optional aspect relate to the system and computer-implemented method of using, e.g., applying, the prediction model.

Optionally, the processor subsystem of the system using the prediction model is further configured to:

apply the segmentation algorithm to the input image data, thereby obtaining the segmentation of the boundary in the input image data; and identify the image portions to which the prediction model is to be applied on the basis of the image portions containing part of the boundary.

Although it is not needed per se for the segmentation algorithm to be applied to the input image data for the purpose of predicting the correctness of the segmentation, the segmentation allows image portions to be identified for which the correctness of the segmentation is to be determined. Namely, the boundary is typically only present in a subset of image portions. To reduce the processing time or to reduce the occurrence of irrelevant predictions of correctness, the prediction model may be applied to only a subset of the image portions of the input image data, namely to those which contain the boundary to be segmented. The segmentation at least coarsely identifies the boundary. As such, the segmentation may be used to select the image portions to which the prediction model is to be applied.

Optionally, the input image data is 3D image data, the segmentation algorithm provides a 3D segmentation of the boundary in the input image data, and the processor subsystem is configured to identify the image portions to which the prediction model is to be applied as sub-volumes of the 3D image data which are centred around respective parts of the 3D segmentation. 3D image data is highly relevant in clinical practice. The prediction model may be trained on, and applied to, sub-volumes of 3D image data to predict the correctness of the segmentation in each sub-volume if the segmentation algorithm is applied to the 3D image data.

Optionally, the processor subsystem is configured to generate the output data as output image data containing a visualization of the correctness of the segmentation. The correctness of the segmentation may be visualized, e.g., as an output image which may be stored as a file, displayed on a display, etc. For example, the output image data may contain the visualization of the correctness of the segmentation as an overlay over a visualization of the segmentation itself. For example, the output image data may visualize the adapted mesh and indicate the correctness of the segmentation by applying a color coding to parts of the mesh, e.g., as a colormap from red to green, e.g., from 'incorrect' to 'correct'.

Optionally, the processor subsystem is configured to adjust the visualization of the segmentation of the boundary to visually highlight one or more image portions in which the boundary is considered to be incorrectly segmented in accordance with a segmentation quality criterion.

Optionally, the processor subsystem is configured to:

execute a clinical application which uses the segmentation of the boundary by the segmentation algorithm; and adjust a workflow of the clinical application on the basis of the correctness of the segmentation.

In accordance with a further aspect of the invention, either or both systems are comprised in, or implemented by, a workstation or imaging apparatus.

In accordance with a further aspect of the invention, a computer-readable medium is provided comprising transitory or non-transitory data representing instructions arranged to cause a processor system to perform either or both computer-implemented methods.

In accordance with a further aspect of the invention, a computer-readable medium is provided comprising transitory or non-transitory data representing a prediction model which is trained to predict a correctness of segmentation by a segmentation algorithm, wherein the prediction model is trained on labelled image portions of training image data, wherein labels of the labelled image portions are indicative of a correctness of segmentation by a segmentation algorithm of a boundary in the respective image portion.

It will be appreciated by those skilled in the art that two or more of the above-mentioned embodiments, implementations, and/or optional aspects of the invention may be combined in any way deemed useful.

Modifications and variations of any computer-implemented method and/or any computer program product, which correspond to the described modifications and variations of a corresponding system, can be carried out by a person skilled in the art on the basis of the present description.

BRIEF DESCRIPTION OF THE DRAWINGS

These and other aspects of the invention will be apparent from and elucidated further with reference to the embodiments described by way of example in the following description and with reference to the accompanying drawings, in which.

It should be noted that the figures are purely diagrammatic and not drawn to scale. In the figures, elements which correspond to elements already described may have the same reference numerals.

LIST OF REFERENCE NUMBERS

The following list of reference numbers is provided for facilitating the interpretation of the drawings and shall not be construed as limiting the claims.

020, 022 data storage
030 training image data
040 label data
050 model data
060 input image data
070 output data
080 user input device
082 user input data
100 system for generating prediction model
120 data interface
122, 124 data communication
140 processor subsystem
200 system for predicting correctness of segmentation
220 data interface
222, 224 data communication
240 processor subsystem
242 output data
260 user interface subsystem
262 display data
280 display
300 medical image
310 anatomical structure
320 boundary of anatomical structure
330 segmentation by algorithm
340 manually corrected segmentation
342 correction action
350 image portion
360 distance between segmentations
380 visualization of correctness, overlay
382 warning dialog
400 method of generating prediction model
410 accessing training image data, labels
420 training prediction model
430 outputting model data representing prediction model
500 method of predicting correctness of segmentation
510 accessing model data, input image data
520 applying prediction model to input image data
530 outputting correctness of segmentation
600 computer-readable medium
610 non-transitory data

DETAILED DESCRIPTION OF EMBODIMENTS

Figure 1:
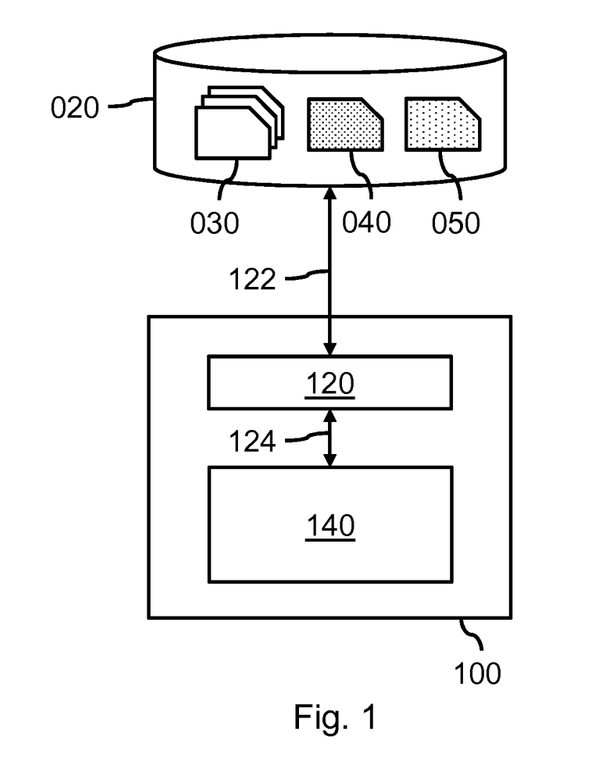
FIG. 1 shows a system for generating a prediction model for predicting a correctness of segmentation by a segmentation algorithm.

FIG. 1 shows a system 100 for generating a prediction model for predicting a correctness of segmentation by a segmentation algorithm. The system 100 may comprise a data interface 120 and a processor subsystem 140 which may internally communicate via data communication 124. The processor subsystem 140 may be configured to, during operation of the system 100 and using the data interface 120, access training image data 030 and labels 040 for respective image portions of the training image data, wherein the labels are obtained by applying the segmentation algorithm to the training image data, wherein the labels are indicative of a correctness of the segmentation of a boundary in the respective image portion by the segmentation algorithm. For example, as shown in FIG. 1, the data interface 120 may provide access 122 to an external data storage 020 which may comprise said data 030, 040. Alternatively, the data 030, 040 may be accessed from an internal data storage which is part of the system 100. Alternatively, the data 030, 040 may be received via a network from another entity. In general, the data interface 120 may take various forms, such as a network interface to a local or wide area network, e.g., the Internet, a storage interface to an internal or external data storage, etc. The data storage 020 may take any known and suitable form.

The processor subsystem 140 may be further configured to, during operation of the system 100, train the prediction model using a machine learning technique and using said labelled image portions as input, and output model data 050 representing the trained prediction model. The model data 050 may be stored by the system 100 in the data storage 020 or elsewhere, sent via a network, etc. For example, the model data 050 may be provided to another entity such as the system 200 of FIG. 2 for use in predicting a correctness of segmentation by a segmentation algorithm. In some embodiments, the model data 050 may be associated or associable with the segmentation algorithm, e.g., by the model data 050 containing an identifier of the segmentation algorithm, by containing a reference to data representing the segmentation algorithm, by being stored with or as part of a data container containing the data representing the segmentation algorithm, etc.

Various details and aspects of the operation of the system 100, including optional aspects, will be further elucidated elsewhere in this specification.

In general, the system 100 may be embodied as, or in, a single device or apparatus, such as a workstation, e.g., laptop or desktop-based, or a server. The device or apparatus may comprise one or more microprocessors which execute appropriate software. For example, the processor subsystem may be embodied by a single Central Processing Unit (CPU), but also by a combination or system of such CPUs and/or other types of processing units. The software may have been downloaded and/or stored in a corresponding memory, e.g., a volatile memory such as RAM or a non-volatile memory such as Flash. Alternatively, the functional units of the system, e.g., the data interface and the processor subsystem, may be implemented in the device or apparatus in the form of programmable logic, e.g., as a Field-Programmable Gate Array (FPGA). In general, each functional unit of the system may be implemented in the form of a circuit. It is noted that the system 100 may also be implemented in a distributed manner, e.g., involving different devices or apparatuses, such as distributed servers, e.g., in the form of cloud computing.

With continued reference to the training of the prediction model, it is noted that the labels 040 may be obtained in various ways. For example, the segmentation algorithm may have been previously applied to the training image data 030 and the resulting segmentations have been manually inspected, e.g., by one or more users. The labels 040 may then have been generated in any suitable manner, including but not limited to those known from the field of image annotation. For example, the user(s) may use a graphical user interface to assign the labels, with the software which provides the graphical user interface then generating the labels 040 in a computer-readable form and in a manner in which the labels are associated or associable with the respective image portions of the training image data 030.

Another example is that the labels 040 may have been generated automatically or semi-automatically, by the system 100 itself or by another entity. An example of the former may be the following, which is also described elsewhere in this specification with reference to FIG. 6. The system 100 may obtain first segmentation data representing the segmentation of the boundary in the respective image portions by the segmentation algorithm, and second segmentation data representing a corrected segmentation of the boundary in the respective image portions by a user. Effectively, the first segmentation data may represent an automatic segmentation of the training image data 030 by the segmentation algorithm, and the second segmentation data may represent a manually reviewed, and if needed, corrected version thereof. The correctness of segmentation may then be determined by the system 100, or specifically the processor subsystem 140, by comparing the first segmentation data with the second segmentation data. For example, the correctness may be determined by determining a distance between corresponding parts of the respective segmentations of the boundary. Here, 'corresponding' may refer to an anatomical correspondence, and/or if the segmentation is comprised of parts such as mesh parts, a correspondence in segmentation part. Namely, if the distance is zero, it may be assumed that no correction took place, which may be an indication that the original segmentation was correct. Conversely, if there is a non-zero distance, this may indicate that a correction took place. In such a case, the distance between mesh parts may be indicative of the quality of the original segmentation, as a large distance may represent a large correction and may indicate an originally poor segmentation, whereas a small distance may represent a small correction and may indicate an originally imperfect, but perhaps still reasonable segmentation. Effectively, the distance may be indicative of a severity of the correction which in turn may be indicative of a quality of the original segmentation by the segmentation algorithm.

The labels 040 may then be assigned by the system 100 based on the determined distance between corresponding parts of the segmentations. For example, the labels may be assigned as "corrected" or "uncorrected", or by categories such as "correction distance below 0.5 mm", "correction distance between 0.5 and 1.0 mm", etc. In some embodiments, the distance, e.g., as expressed in millimetres, may be used directly as the label for a respective image portion.

In some embodiments, the system 100 may itself generate the first segmentation data, e.g., by accessing a data representation of the segmentation algorithm and by applying the segmentation algorithm to the training image data 030. The second segmentation data may be obtained by the system 100 based on user input provided by user via a user interface subsystem, such as the one elucidated with reference to FIG. 2. The user interface subsystem may enable the user to review the segmentation obtained by the segmentation algorithm and, if needed, correct it.

Figure 2:
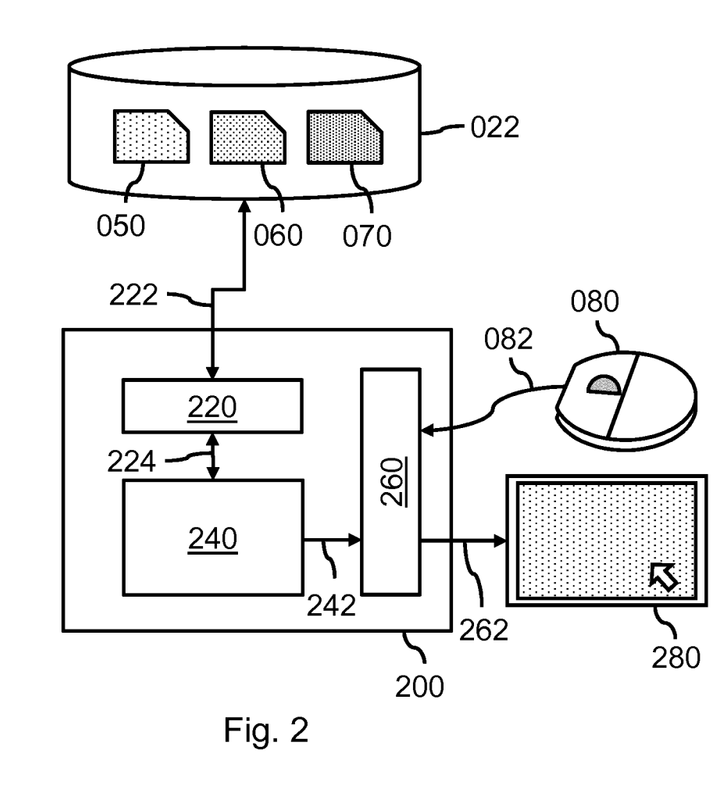
FIG. 2 shows a system for using the prediction model to predict the correctness of segmentation by the segmentation algorithm.

FIG. 2 shows a system 200 for using the prediction model to predict a correctness of segmentation by the segmentation algorithm when the segmentation algorithm is applied to non-training input image data. The system 200 may comprise a data interface 220 and a processor subsystem 240 which may internally communicate via data communication 224. The processor subsystem 240 may be configured to, during operation of the system 200 and using the data interface 220, access the model data 050 as described with reference to FIG. 1, as well as input image data 060 which contains a boundary to be segmented by the segmentation algorithm. For example, as also shown in FIG. 2, the data interface 220 may provide access 222 to an external data storage 022 which comprises said data 050, 060. Alternatively, the data 050, 060 may be accessed from an internal data storage. Alternatively, the data 050, 060 may be received via a network. In general, the data interface 220 may take various forms, such as a network interface to a local or wide area network, e.g., the Internet, a storage interface to an internal or external data storage, etc. The data storage 022 may take any known and suitable form.

The processor subsystem 240 may be further configured to, during operation of the system 200, apply the prediction model to respective image portions of the input image data 060 to predict the correctness of the segmentation of the boundary in the respective image portions by the segmentation algorithm, and to generate output data indicative of the correctness of segmentation to enable an incorrect segmentation of the boundary by the segmentation algorithm to be identified on the basis of the output data. For example, the output data 070 may take the form of file which is stored in the data storage 022 or elsewhere. In some embodiments, the output data 070 may be output image data containing a visualization of the correctness of the segmentation. In some embodiments, the visualization of the correctness of the segmentation may be generated by the system 200 as an overlay over a visualization of the segmentation of the boundary.

As an optional component, the system 200 may comprise a user interface subsystem 260 which may be configured to, during operation of the system 200, enable a user to interact with the system 200, for example using a graphical user interface. The user interface subsystem 260 may comprise a user input interface (not separately shown in FIG. 2) which may be configured to receive user input data 082 from a user input device 080 operable by the user. The user input device 080 may take various forms, including but not limited to a computer mouse, touch screen, keyboard, microphone, etc. FIG. 2 shows the user input device to be a computer mouse 080. In general, the user input interface may be of a type which corresponds to the type of user input device 080, i.e., it may be a thereto corresponding type of user device interface. The user interface subsystem 260 may further comprise a display output interface (not separately shown in FIG. 2) for outputting the output data 242 to a rendering device, such as a display 280. For example, the display output interface may generate display data 262 for the display 280 which causes the display 280 to render the output data 242 in a sensory perceptible manner. For example, if the output data 242 is output image data, the display output interface may display the output image data 242 on the display.

In general, the system 200 may be embodied as, or in, a single device or apparatus, such as a workstation, e.g., laptop or desktop-based, or a mobile device. The device or apparatus may comprise one or more microprocessors which execute appropriate software. For example, the processor subsystem may be embodied by a single Central Processing Unit (CPU), but also by a combination or system of such CPUs and/or other types of processing units. The software may have been downloaded and/or stored in a corresponding memory, e.g., a volatile memory such as RAM or a non-volatile memory such as Flash. Alternatively, the functional units of the system, e.g., the data interface and the processor subsystem, may be implemented in the device or apparatus in the form of programmable logic, e.g., as a Field-Programmable Gate Array (FPGA). In general, each functional unit of the system may be implemented in the form of a circuit. It is noted that the system 200 may also be implemented in a distributed manner, e.g., involving different devices or apparatuses, such as the client and server of a client-server implementation.

Figure 3:
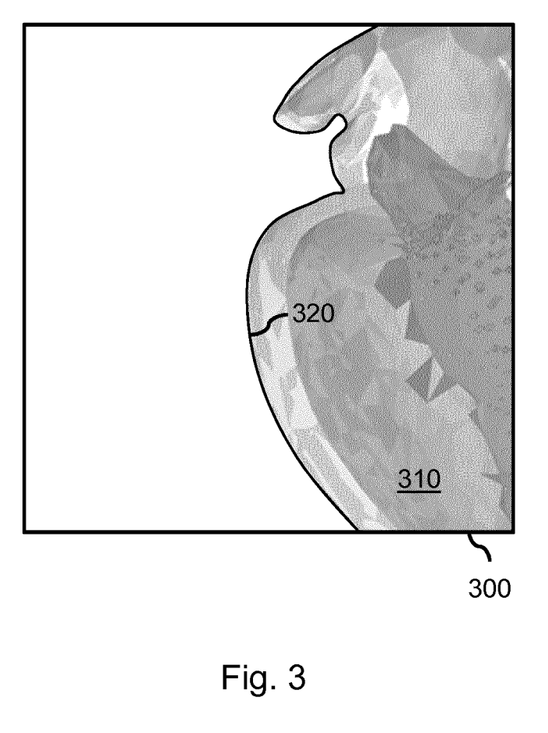
FIG. 3 shows a medical image showing an anatomical structure of which the boundary is to be segmented by a segmentation algorithm.

FIG. 3 shows a schematic representation of a medical image 300 showing part of an anatomical structure 310, being in this example part of the heart, of which the boundary 320 is to be segmented by a segmentation algorithm.

It is noted that for sake of illustration and legibility, the anatomical structure 310 is shown in FIG. 3 and elsewhere in the form of a 3D model of the heart rather than by actual image data. It will be appreciated, however, that typically the segmentation algorithm is applied to the actual image data, and in fact, that the 3D model is typically rather the result of a segmentation by a particular type of segmentation algorithm, namely a model-based segmentation algorithm.

Figure 4:
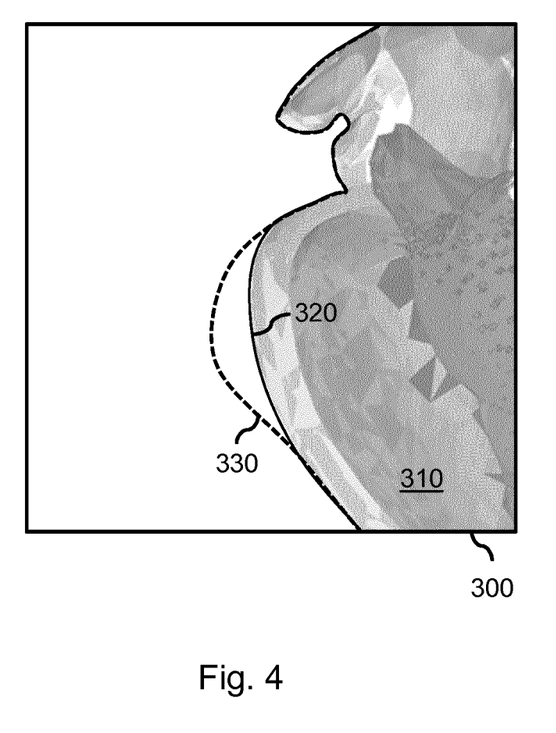
FIG. 4 shows a result of a segmentation of the boundary of the anatomical structure by the segmentation algorithm, in which at least part of the boundary has been incorrectly segmented by the segmentation algorithm.

FIG. 4 shows a segmentation 330 of the boundary 320 of the anatomical structure 310 by the segmentation algorithm. The segmentation 330 is shown here and elsewhere by a dashed line, which may correspond to a segmentation surface established by the segmentation algorithm. A non-limiting example of such a segmentation surface is the segmentation surface formed by a mesh model which is applied to the image data of the anatomical structure 310. As can be seen in FIG. 4, at least part of the boundary 320 has been incorrectly segmented by the segmentation algorithm, in that the segmentation 330 locally extends beyond the actual boundary 320. Such incorrect segmentations may be due to various reasons, e.g., due to limitations in the segmentation algorithm, e.g., because of imperfections in the heuristics, under-training of a trained segmentation, etc. Another reason is that the particular shape of the anatomical structure may not conform to an excepted shape by the segmentation algorithm, e.g., the medical image may be considered 'out-of-spec' for the segmentation algorithm, etc. It will be appreciated that various other types of 'incorrect segmentations' exist as well.

Figure 5:
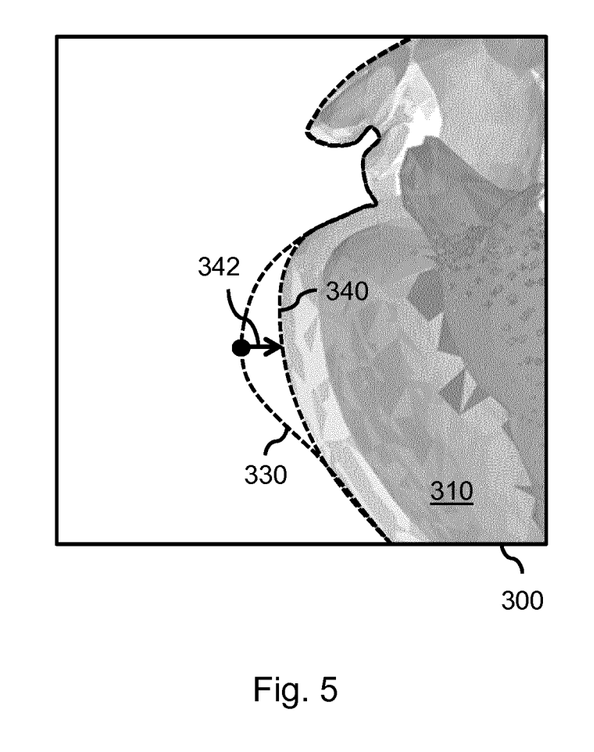
FIG. 5 illustrates a manual correction of the segmentation.

FIG. 5 illustrates a manual correction of the segmentation 330 of FIG. 4, as may be performed by a user, for example during review of the segmentation 330 of FIG. 4. As a result of the correction, which is schematically indicated in FIG. 5 by an arrow 342, a corrected segmentation 340 may be obtained which may better match the actual boundary of the anatomical structure 310. Such correction may be applied in various ways as described elsewhere in this specification.

Figure 6:
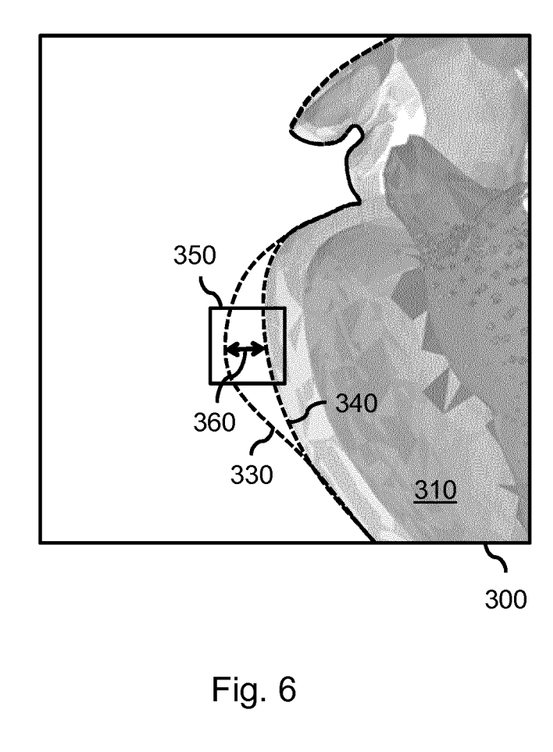
FIG. 6 shows a segmentation obtained by the segmentation algorithm, a corrected segmentation and a distance between both segmentations; the distance may be used as a label which is indicative of the correctness of segmentation together with local image data as input to the training of the prediction model.

FIG. 6 illustrates how the correctness of the original segmentation 330 by the segmentation algorithm may be determined from the original segmentation 330 and the corrected segmentation 340. Namely, the local distance 360 between both segmentations may be considered to be indicative of the local 'correctness' of segmentation. This distance may be used to locally label the image data, e.g., in an image portion 350. The labelled image data may then be used as training data in the training of the prediction model, e.g., as described with reference to FIG. 1 and elsewhere. For example, if the segmentation 330 is a mesh, the geometric distance between corresponding mesh portions of both segmentations 330, 340 may be determined, and the geometric distance may be used as a label for the image data within a local neighbourhood 350 of the mesh portion. This process may be repeated for a set of image portions to obtain the labelled training image data.

Figure 7A:
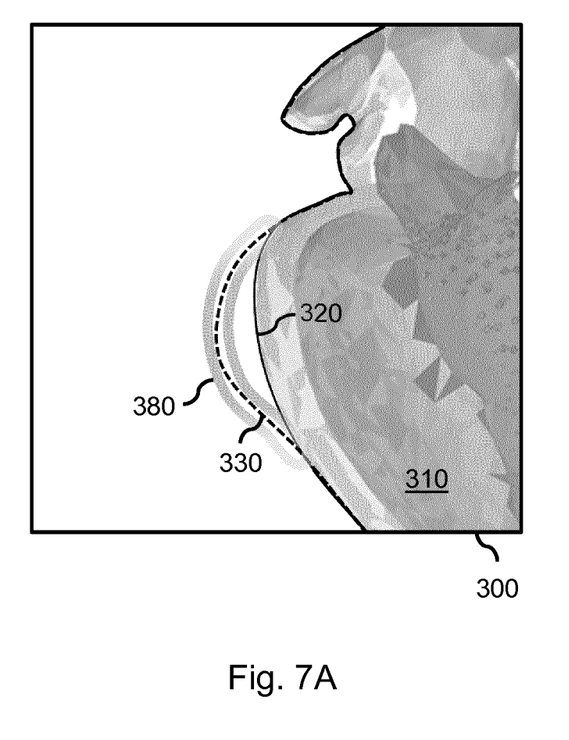
FIG. 7A illustrates a subsequent use of the prediction model to predict the correctness of the segmentation by the segmentation algorithm, which results in an overlay being displayed indicating the incorrectness of the segmentation.

FIG. 7A shows a subsequent use of the prediction model to predict the correctness of the segmentation by the segmentation algorithm. For sake of illustration, a same medical image 300, anatomical structure 310 and boundary 320 are shown as previously in FIGS. 3-6. It will be appreciated, however, that while in FIGS. 3-6 the medical image 300 is shown for the purpose of generating labels and training the prediction model, and may thus be part of the training image data, the prediction model is typically used after training with other 'non-training' image data.

As shown in FIG. 7A, the prediction model may be applied to the medical image 300 to determine the correctness of the segmentation 330 of the boundary in the respective image portions by the segmentation algorithm. It is noted that while FIG. 7A shows the segmentation 330, such a prediction may be obtained without having the segmentation 330 actually available, but rather (only) using the image data of the medical image 300 as input. As output, a labelling of image portions of the medical image 300 may be obtained. This labelling may take a same or similar form as the labelling on which the prediction model was trained, e.g., as binary labels, non-binary labels, etc. Continuing the example of FIG. 6, the labels may also indicate a distance of correction. This distance may be used to generate a color-coded overlay 380 (which is reproduced in greyscales in FIG. 7A for reproducibility reasons) over or next to a visualization of the segmentation 330. For example, the color-coding may indicate the degree of correctness.

Figure 7B:
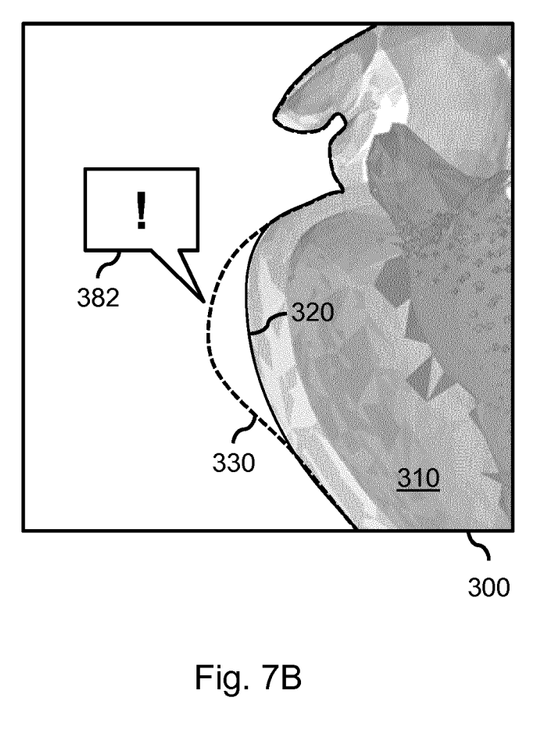
FIG. 7B shows a warning dialog being displayed next to the visualization of the segmentation indicating the incorrectness of the segmentation.

Various other visualization options are equally conceivable. For example, the visualization of the segmentation 330 itself may be color-coded, e.g., by color-coding mesh triangles. The color-coding may be binary: correction required or not. The color-coding may also indicate the probability of the correction necessity, for example by coding parts of the mesh 'green' where no correction is needed, and coding parts of the mesh 'red' where there is a high probability of needing correction. The color-coding may indicate the predicted correction distance. As another example, FIG. 7B shows a warning dialog 382, indicating the incorrectness of the segmentation, being displayed next to the visualization of the segmentation. Such a warning dialog 382 may be presented if the segmentation is considered to necessitate correction, e.g., if the predicted correction distance exceeds a threshold.

A particular embodiment may be the following, which is based on 3D model-based segmentation using meshes. The training of the prediction model may use a number of previously corrected segmentation results. If the segmentation algorithm is comparatively robust and reliable, a large number of such segmentation results may be desirable. If such results are available, the training may be performed once (and off-line) for a segmentation algorithm, with the resulting prediction model then being stored and used for new patient cases. The prediction model may be adapted and learn over time by re-training using data sets previously processed, segmented and corrected in a clinical application. In some embodiments, the training of the prediction model may be performed in a clinical setting, e.g., by the same system which applies the prediction model. Such type of training may also allow the prediction model to learn correction preferences, e.g., of specific users.

For the generation of the training samples, which together represent the training image data, a medical image, an automatic segmentation result by the segmentation algorithm and a manual corrected segmentation result may be used. For example, for each patient case and for a center of each mesh triangle, an image sample of a suitable size, e.g., an image portion such as a 3D sub-volume, may be extracted. In addition, the distance between the triangle centers of the automatic segmented mesh and corrected mesh may be calculated. In case of identity, the image sample may be labelled "uncorrected" or "does not need correction", otherwise the image sample may be labelled "corrected" or "needs correction".

The prediction model may for example be a Convolutional Neural Network which is trained for each triangle center on all patient cases using the categories mentioned above and using known deep learning tools and environments such as the Microsoft Cognitive Toolkit (CNTK) or the Caffe Deep Learning Framework. If needed, an initial set of training image data may be augmented by rotating and deforming images together with the corresponding (automatic) and manually corrected segmentation result. Data augmentation may also be done by artificially displacing contours and automatically generating 'manual' corrections.

During use of the prediction model, the list of mesh triangles which are predicted to need correction may be compared to the corrected mesh triangles or to the mesh triangles already shown to the user. In case that not all triangles from the list are corrected or displayed, the correction workflow may indicate those triangles to the user in a suitable way to the user, e.g., by a warning dialog, by the view of the segmentation being automatically adjusted to view these triangles, etc.

It will be appreciated that although the above embodiments refer to segmentation by mesh models, triangles, etc, the above-mentioned techniques may also be applied to any other type of segmentation of a boundary in an image.

Figure 8:
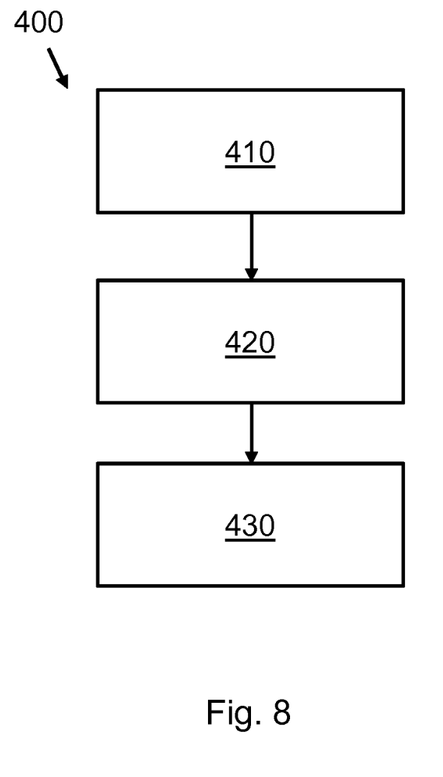
FIG. 8 shows a method for generating a prediction model for predicting a correctness of segmentation by a segmentation algorithm.

FIG. 8 shows a block-diagram of computer-implemented method 400 for generating a prediction model for predicting a correctness of segmentation by a segmentation algorithm. The method 400 may correspond to an operation of the system 100 of FIG. 1. However, this is not a limitation, in that the method 400 may also be performed using another system, apparatus or device.

The method 400 may comprise, in an operation titled "ACCESSING TRAINING IMAGE DATA, LABELS", accessing 410 training image data and labels for respective image portions of the training image data, wherein the labels are obtained by applying the segmentation algorithm to the training image data, wherein the labels are indicative of a correctness of the segmentation of a boundary in the respective image portion by the segmentation algorithm. The method 400 may further comprise, in an operation titled "TRAINING PREDICTION MODEL", training 420 the prediction model using a machine learning technique and using said labelled image portions as input. The method 400 may further comprise, in an operation titled "OUTPUTTING MODEL DATA REPRESENTING PREDICTION MODEL", outputting 430 model data representing the trained prediction model.

Figure 9:
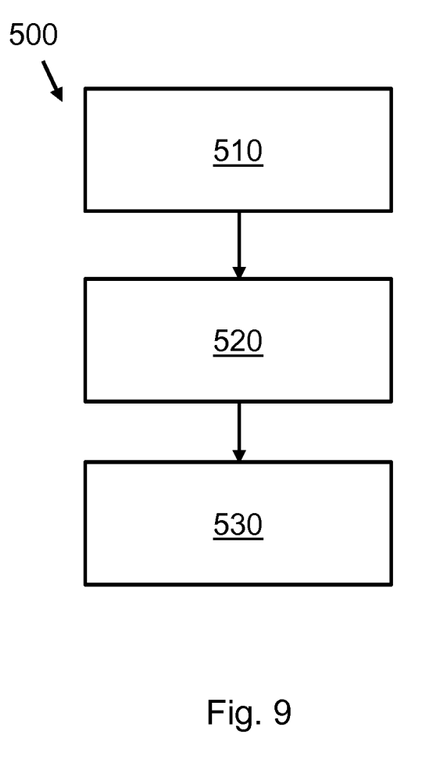
FIG. 9 shows a method for using the prediction model to predict the correctness of segmentation by the segmentation algorithm.

FIG. 9 shows a block-diagram of computer-implemented method 500 for using the prediction model to predict the correctness of segmentation by the segmentation algorithm. The method 500 may correspond to an operation of the system 200 of FIG. 2. However, this is not a limitation, in that the method 500 may also be performed using another system, apparatus or device.

The method 500 may comprise, in an operation titled "ACCESSING MODEL DATA, INPUT IMAGE DATA", accessing 510 model data representing a prediction model which is trained on labelled image portions of training image data, wherein labels of the labelled image portions are indicative of a correctness of segmentation of a boundary in the respective image portion by the segmentation algorithm, and input image data containing a boundary to be segmented by the segmentation algorithm. The method 500 may further comprise, in an operation titled "APPLYING PREDICTION MODEL TO INPUT IMAGE DATA", applying 520 the prediction model to respective image portions of the input image data to predict the correctness of the segmentation of the boundary in the respective image portions by the segmentation algorithm. The method 500 may further comprise, in an operation titled "OUTPUTTING CORRECTNESS OF SEGMENTATION", generating 530 output data indicative of the correctness of segmentation to enable an incorrect segmentation of the boundary by the segmentation algorithm to be identified on the basis of the output data.

It will be appreciated that, in general, the operations of method 400 of FIG. 8 and/or method 500 of FIG. 9 may be performed in any suitable order, e.g., consecutively, simultaneously, or a combination thereof, subject to, where applicable, a particular order being necessitated, e.g., by input/output relations.

Figure 10:
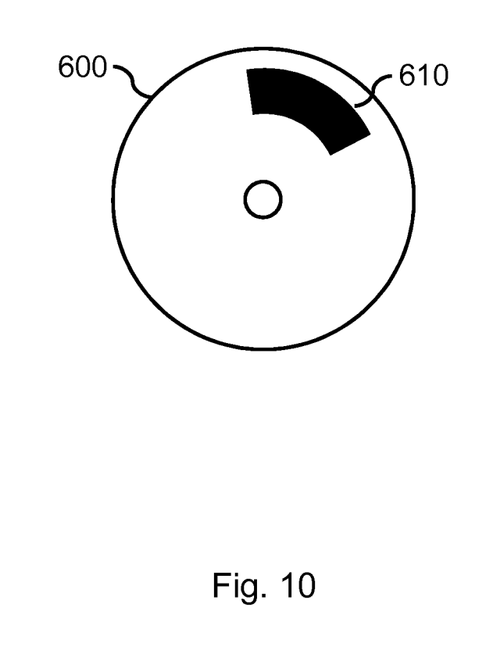
FIG. 10 shows a computer-readable medium comprising data.

The method(s) may be implemented on a computer as a computer implemented method, as dedicated hardware, or as a combination of both. As also illustrated in FIG. 10, instructions for the computer, e.g., executable code, may be stored on a computer readable medium 600, e.g., in the form of a series 610 of machine readable physical marks and/or as a series of elements having different electrical, e.g., magnetic, or optical properties or values. The executable code may be stored in a transitory or non-transitory manner. Examples of computer readable mediums include memory devices, optical storage devices, integrated circuits, servers, online software, etc. FIG. 10 shows an optical disc 600. Alternatively, the computer readable medium 600 may comprise transitory or non-transitory data 610 representing the prediction model as described elsewhere in this specification.

Examples, embodiments or optional features, whether indicated as non-limiting or not, are not to be understood as limiting the invention as claimed.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. Expressions such as "at least one of" when preceding a list or group of elements represent a selection of all or of any subset of elements from the list or group. For example, the expression, "at least one of A, B, and C" should be understood as including only A, only B, only C, both A and B, both A and C, both B and C, or all of A, B, and C. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for generating a prediction model for predicting a correctness of segmentation by a segmentation algorithm, the system comprising:
   a data interface for accessing:
      training image data; and
      labels for respective image portions of the training image data, wherein the labels are obtained by applying the segmentation algorithm to the training image data, wherein the labels are indicative of a correctness of the segmentation of a boundary in the respective image portion by the segmentation algorithm; and
   a processor subsystem configured to:
      train the prediction model using a machine learning technique and using said labelled image portions as input; and
      output model data representing the trained prediction model, wherein the processor subsystem is further configured to generate the labels for the respective image portions by:
         via the data interface, accessing:
            first segmentation data representing the segmentation of the boundary in the respective image portions by the segmentation algorithm;
            second segmentation data representing a corrected segmentation of the boundary in the respective image portions by a user;
         determining the correctness of segmentation by comparing the first segmentation data with the second segmentation data; and
         assigning the labels which are indicative of the correctness of segmentation to the respective image portions.

2. The system according to claim 1, wherein the processor subsystem is configured to determine the correctness of the segmentation by the segmentation algorithm for an image portion based on a distance between corresponding parts of the respective segmentations of the boundary.

3. A workstation or imaging apparatus comprising the system according to claim 1.

4. A system for predicting a correctness of segmentation by a segmentation algorithm, the system comprising:
   a processor subsystem configured to:
      identify image portions to which a prediction model is to be applied on the basis of the image portions containing part of a boundary;
      apply the prediction model to respective image portions of an input image data to predict the correctness of the segmentation of the boundary in the respective image portions by the segmentation algorithm; and
      generate output data indicative of the correctness of the segmentation to enable an incorrect segmentation of the boundary by the segmentation algorithm to be identified on the basis of the output data.

5. The system according to claim 4, wherein the processor subsystem is further configured to:
   apply the segmentation algorithm to the input image data, thereby obtaining the segmentation of the boundary in the input image data.

6. The system according to claim 5, wherein:
   the input image data is 3D image data;
   the segmentation algorithm provides a 3D segmentation of the boundary in the input image data; and
   the processor subsystem is configured to identify the image portions to which the prediction model is to be applied as sub-volumes of the 3D image data which are centred around respective parts of the 3D segmentation.

7. The system according to claim 4, wherein the processor subsystem is configured to generate the output data as output image data containing a visualization of the correctness of the segmentation.

8. The system according to claim 7, wherein the output image data contains the visualization of the correctness of the segmentation as an overlay over a visualization of the segmentation of the boundary.

9. The system according to claim 4, wherein the processor subsystem is configured to adjust a visualization of the segmentation of the boundary to visually highlight one or more image portions in which the boundary is considered to be incorrectly segmented in accordance with a segmentation quality criterion.

10. The system according to claim 4, wherein the processor subsystem is configured to:
   execute a clinical application which uses the segmentation of the boundary by the segmentation algorithm; and
   adjust a workflow of the clinical application on the basis of the correctness of the segmentation.

11. A non-transitory computer-readable medium comprising data representing a prediction model which is trained to predict a correctness of segmentation by a segmentation algorithm, wherein the prediction model is trained on labelled image portions of training image data, wherein labels of the labelled image portions are indicative of the correctness of the segmentation by the segmentation algorithm of a boundary in the respective image portion, wherein the labels comprise a distance value or color coding that is indicative of the correctness.

12. A computer-implemented method of predicting a correctness of segmentation by a segmentation algorithm, the method comprising:
accessing:
  model data representing a prediction model which is trained on labelled image portions of training image data, wherein labels of the labelled image portions are indicative of a correctness of segmentation of a boundary in the respective image portion by the segmentation algorithm; and
  input image data containing a boundary to be segmented by the segmentation algorithm;
applying the prediction model to respective image portions of the input image data to predict the correctness of the segmentation of the boundary in the respective image portions by the segmentation algorithm;
generating output data indicative of the correctness of segmentation to enable an incorrect segmentation of the boundary by the segmentation algorithm to be identified on the basis of the output data; and
adjusting a visualization of the segmentation of the boundary to visually highlight one or more image portions in which the boundary is considered to be incorrectly segmented in accordance with a segmentation quality criterion.

13. A computer-implemented method of generating a prediction model for predicting a correctness of segmentation by a segmentation algorithm, the method comprising:
accessing:
  training image data;
  labels for respective image portions of the training image data, wherein the labels are obtained by applying the segmentation algorithm to the training image data, wherein the labels are indicative of a correctness of the segmentation of a boundary in the respective image portion by the segmentation algorithm;
training the prediction model using a machine learning technique and using said labelled image portions as input; and
outputting model data representing the trained prediction model.

14. A non-transitory computer-readable medium comprising data representing instructions arranged to cause a processor system to perform the computer-implemented method according to claim 13.

* * * * *